United States Patent [19]

Posin

[11] Patent Number: 5,069,209
[45] Date of Patent: Dec. 3, 1991

[54] ELECTRICAL TERMINAL

[75] Inventor: Jack Posin, Allawah, Australia

[73] Assignee: Telectronics Pacing Systems, Inc., Englewood, Colo.

[21] Appl. No.: 586,772

[22] Filed: Sep. 21, 1990

[51] Int. Cl.$^5$ .............................................. A61N 1/02
[52] U.S. Cl. ................................................ 128/419 P
[58] Field of Search .................................. 128/419 P

[56] References Cited

U.S. PATENT DOCUMENTS

| | | | |
|---|---|---|---|
| 3,606,881 | 9/1971 | Woodson | 128/419 P |
| 4,012,103 | 3/1977 | Lunquist | 128/419 P |
| 4,112,953 | 9/1978 | Shanker et al. | 128/419 P |
| 4,202,592 | 3/1980 | Rullier et al. | 128/419 P |
| 4,347,849 | 9/1982 | Congdon | 128/419 P |
| 4,466,441 | 8/1984 | Skubitz et al. | 128/419 P |
| 4,541,681 | 9/1985 | Dorman et al. | 339/100 |
| 4,672,979 | 6/1987 | Pohndorf | 128/784 |
| 4,784,141 | 11/1988 | Peers-Trevarton | 128/419 P |
| 4,848,346 | 7/1989 | Crawford | 128/419 P |
| 4,942,876 | 7/1990 | Gotthardt | 128/419 P |

*Primary Examiner*—William E. Kamm
*Attorney, Agent, or Firm*—Gottlieb, Rackman & Reisman

[57] ABSTRACT

A terminal for detachably connecting an electrical lead to an electrical device is disclosed. The terminal includes a stationary support structure adapted to be fixed to the device, and a movable structure adapted to be carried by the stationary support structure for movement between first and second positions relative to the support structure. The movable structure has a plurality of wall members thereon that are movable relatively toward and away from one another between a first spaced apart position less than the diameter of the electrical lead and a second spaced apart position greater than the diameter of the electrical lead for receiving and releasing the lead in the second spaced apart position and for gripping the lead in the first spaced apart position. The terminal further includes a biasing member and a camming device for moving the movable structure between its first and second positions; and, interacting camming members carried by each of the structures and engageable with the camming member on the other of the structures are employed for camming the wall members from one to another of their spaced apart positions.

25 Claims, 4 Drawing Sheets

ELECTRICAL TERMINAL

BACKGROUND OF THE INVENTION

This invention relates to electrical terminals that are used for detachably connecting electrical leads to electrical devices.

The invention will be described herein in connection with its use as a pacemaker terminal for connecting and releasing by hand pressure the proximal end of an electrode lead to an implantable heart pacemaker. However, it will be apparent to those skilled in the art that the invention has broader applicability to electrical terminals generally, irrespective of the device to which the lead is to be connected.

The operation of an implantable heart pacemaker requires the transmission of low level electrical signals generated by the heart to the pacemaker, as well as the pacing voltages generated by the pacemaker to the heart. This physical link of transmission, the pacemaker lead, is a section of high-fatigue-resistant, multi-insulated electrical conductor designed to endure the severe environment inside the human body. Any leakage of body fluids or passage of body ions into the conductor can result in a deterioration of the signals transmitted. The distal end of the lead, in the form of an electrode, provides the fixation to the heart tissue. The proximal end of the lead, in the form of a pin, is connected to the terminal of the pacemaker. The materials used to construct the pacemaker lead must be bio-compatible. For insulation, common selections are silicone rubber, epoxy, or polyurethane. For the conductors, common selections are titanium and its alloys, 316L stainless steel and its derivatives, or platinum and its alloys.

Conventional pacemaker terminals utilize a set screw, or "grub" screw, to secure the proximal pin of the lead. A molded silicone rubber top is used to fully encapsulate the terminal, leaving only a sealable opening for the proximal pin to be inserted through. A small, self-sealing slit is cut in the silicone rubber top above the terminal to allow a custom-designed Allen wrench to gain access to the set screw. The set screw design provides good mechanical locking of the proximal pin, along with electrical continuity between the lead and the terminal.

During an implant operation, the surgeon is required to coat the Allen wrench with a special lubricant, locate the external opening of the self-sealing slit in the silicone rubber top, insert the Allen wrench through the slit, engage the set screw, and tighten the set screw to the appropriate torque. If the surgeon fails to perform any of these procedures successfully, there is a chance that the silicone rubber top or the self-sealing slit might become damaged and fail to provide adequate sealing, thereby allowing body fluids to penetrate through to the terminal. This results in deterioration of the heart signals along with corrosion of the terminal and the proximal pin.

Current, new generation pacemakers require the terminals to be more compact in size and more robust in their use. The existing set screw design, limited by the use of an Allen wrench and a threaded hole configuration, has been found to be inadequate not only with regard to compactness, but also with respect to ease of operation.

A primary object of the invention, therefore, is an improved terminal for providing effortless, positive and secure mechanical and electrical connection of an electrical lead to an electrical device, for example an implantable heart pacemaker.

A further object of the invention is an improved terminal for providing effortless, simple and reliable disconnection of the electrical lead from the electrical device, when required.

Another object of the invention is an improved pacemaker terminal which eliminates the need for the use of any special tools, including a set screw, for connecting and disconnecting the proximal end of an electrode lead to a pacemaker terminal.

A still further object of the invention is to prevent body fluids from penetrating into a pacemaker terminal through Allen wrench slits in the silicone rubber top of a pacemaker case.

Yet another object of the invention is to provide a reduction in the size of the pacemaker terminal, and in the overall dimensions of the silicone rubber top therefore.

SUMMARY OF THE INVENTION

Briefly stated, and in accordance with one embodiment of the invention, there is provided a terminal for detachably connecting an electrical lead to an electrical device. The terminal includes a support structure adapted to be fixed to the device. The terminal further includes a movable structure adapted to be carried by the support structure for movement between first and second positions relative to the support structure. The movable structure includes at least two wall members thereon movable relatively toward and away from one another between a first spaced apart position less than the diameter of the electrical lead and a second spaced apart position greater than the diameter of the electrical lead, for receiving and releasing the lead in the second spaced apart position, and for gripping the lead in the first spaced apart position. The terminal further includes means for moving the movable structure between its first and second positions; and camming means carried by each of the structures and engable with the camming means on the other of the structures for camming the wall members from one to another of their spaced apart positions.

BRIEF DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

DESCRIPTION OF THE PREFERRED EMBODIMENTS

Referring to FIGS. 1-4A, a terminal in accordance with this invention, for use with an implantable heart pacemaker (not shown), has been illustrated generally at 1. The terminal 1 includes a generally cylindrical, stationary support structure or post member, shown generally at 2, and an annular movable structure or collet member, shown generally at 3. The post member 2 is preferably fabricated out of a round rod of bio-compatible metal such as titanium, tivanium, or 316L stainless steel, and includes a pacer end flange 4 that is adapted to be fastened to the titanium top cap of a pacemaker by a brazing process or other permanent joining process. A tranversely extending through hole or aperture 6 is drilled in the upper body 8 of the post member, normal to the cylindrical axis thereof, with a straight bore portion 10 at the entrance thereof and a tapered or conical portion 12 that flares out to a larger diameter at the exit portion thereof. Both the entrance end and the exit end of the aperture 6 are counterbored to provide concentric flat surfaces or side portions 14 and 16 (FIG. 2), respectively, that are normal to the axis of the aperture 6. The side portions 14 and 16 denote the entrance and exit ends, respectively, of the aperture 6. Post member 2 is also provided with a threaded protrusion 18 which extends below the base 4 thereof and thus serves as a convenient connection point for the internal electrical wiring of the pacemaker.

Figure 1:
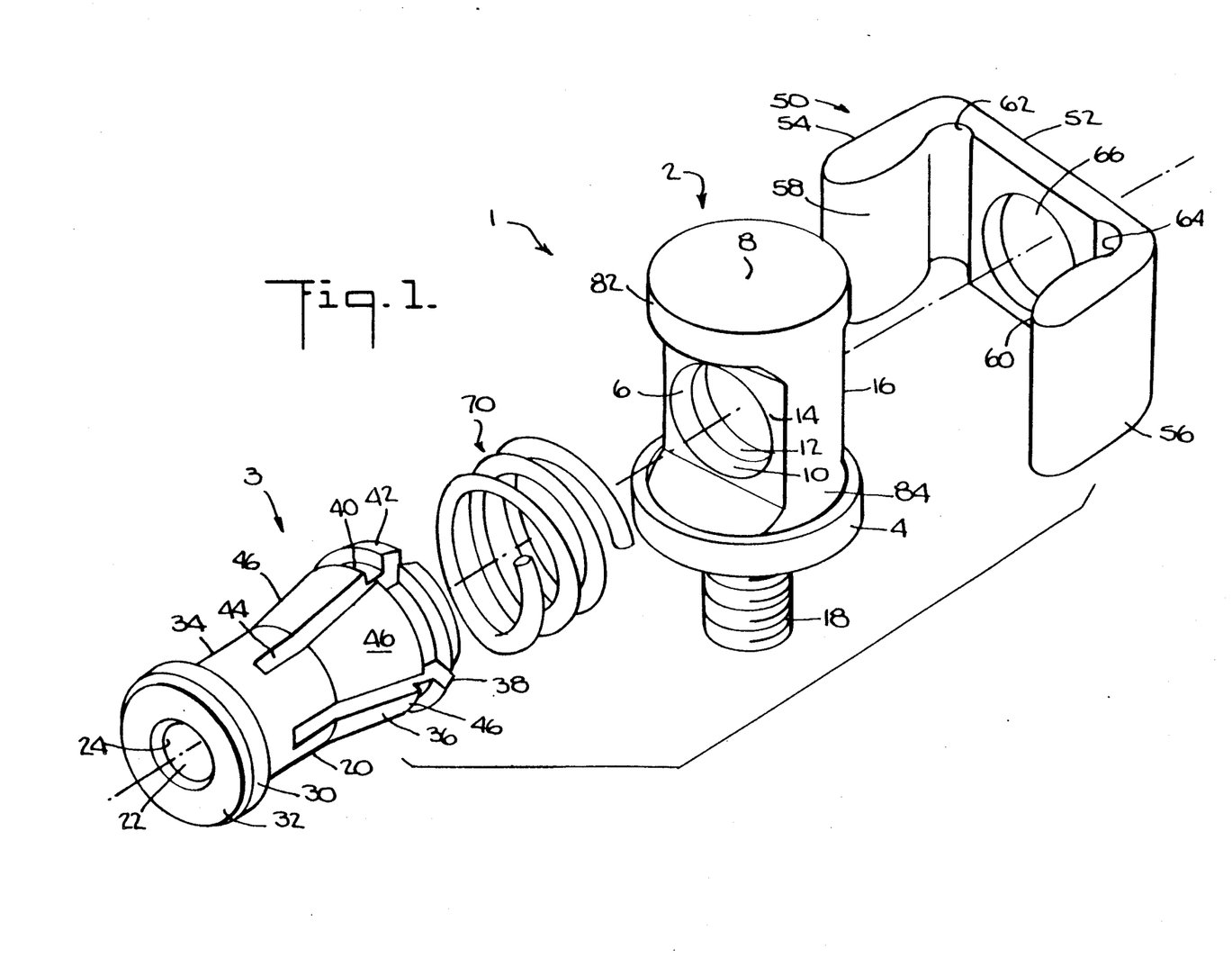
FIG. 1 is an exploded perspective of the invention.

The movable collet member 3 comprises a generally annular section 20 that is fabricated out of a round rod of bio-compatible metal such as that described above in connection with the post member 2. Collet member 3 is also provided with an elongate through hole or aperture, shown generally at 22, which includes an aperture entrance portion 24 and an aperture exit portion 26 therein. The entrance and exit portions 24 and 26 of aperture 22 are essentially of the same diameter, which is slightly larger than the diameter of a middle portion or ridge ring 28 thereof. The ridge ring 28 is made to be just slightly larger in diameter than the diameter of the proximal tip 25 of the electrode lead 23 that is to be received therein, so that the lead can be inserted and removed conveniently when the ring is in its radially expanded, relaxed, condition.

Collet member 3 includes an enlarged flange 30 at one end 32 thereof, followed by a generally cylindrical middle portion 34, which flares out to a generally tapered or conical portion 36 of larger diameter than the cylindrical portion 34. At the other end 38 of the collet member the tapered or generally conical portion 36 of the collet member is provided with a circumferentially extending groove 40 therein which forms a flange 42 immediately adjacent the end 38 of the collet member. In addition, four longitudinal slots 44 are cut radially into the generally conical portion 36 of the collet member. The slots 44 extend from the end 38 into the generally cylindrical middle portion 34 to transform about half of the annular wall of the collet member into four radially movable fingers or wall members 46.

Terminal 1 is also provided with a release member, shown generally at 50. Release member 50 is a generally flat component fabricated from a bio-compatible plastic such as nylon or acetal. Release member 50 is formed in a shallow U-shape that includes a base portion 52, and pair of spaced apart leg portions 54, 56 that are integral with the base portion 52. The leg portions 54, 56 are each provided with respective curved inside camming surfaces 58 and 60, each having the same radius of curvature. In order to increase the flexing capacity of the leg members 54, 56, respective curved grooves 62, 64 are provided at the intersections of the leg portions 54, 56 with the base portion 52 of the release member. A through hole 66, having a straight bore, is provided at the center of the base portion 52.

Terminal 1 is also provided with a spring or biasing means, shown generally at 70. The spring is preferably in the form of a cylindrical coil and is fabricated from a bio-compatible metal similar to that described earlier in connection with the post member 2. Spring 70 is employed to provide a compressive spring force or bias for moving collet member 3 within aperture 6 of post member 2, as will be described in greater detail hereinafter. In addition, the spring member provides electrical continuity between collet member 3 and post member 2 during the use of terminal 1.

The design of terminal 1 requires the assembly of the components to be performed in a particular sequence. First, spring 70 is installed on to the outside cylindrical surface of the middle portion 34 of the collet member. The spring is installed on the middle portion 34 either by being wound thereon, or by sliding it over the conical portion 36 of the collet member when the finger members 46 thereof are radially compressed by a suitable tools (not shown). Next, the collet member 3, with the spring positioned over the middle portion 34 thereof, is pushed through aperture 6 in post member 2 sufficiently for the end 38 thereof to project beyond the side portion 16 of the post member. This is accomplished by first squeezing the four finger members 36 together to reduce the ouside diameter of the tapered section 36 so that the fingers can pass through the smaller diameter at the entrance portion 10 of aperture 6. After the fingers 46 are pushed through the hole 6, with their tips exposed beyond the side portion 16, the release member 50 is installed on to the circumferential groove 40 of the collet member. This is achieved by pushing the tips of the fingers through the hole 66 in release member 50 until the circumferential groove 40 of the collet member engages the perimeter of the hole. Finally, the interlocking of the release member with the collet member is accomplished by opening up the fingers 46 with a pin (not shown) having a smaller diameter than the proximal tip 25 of electrode lead 23.

Figure 2:
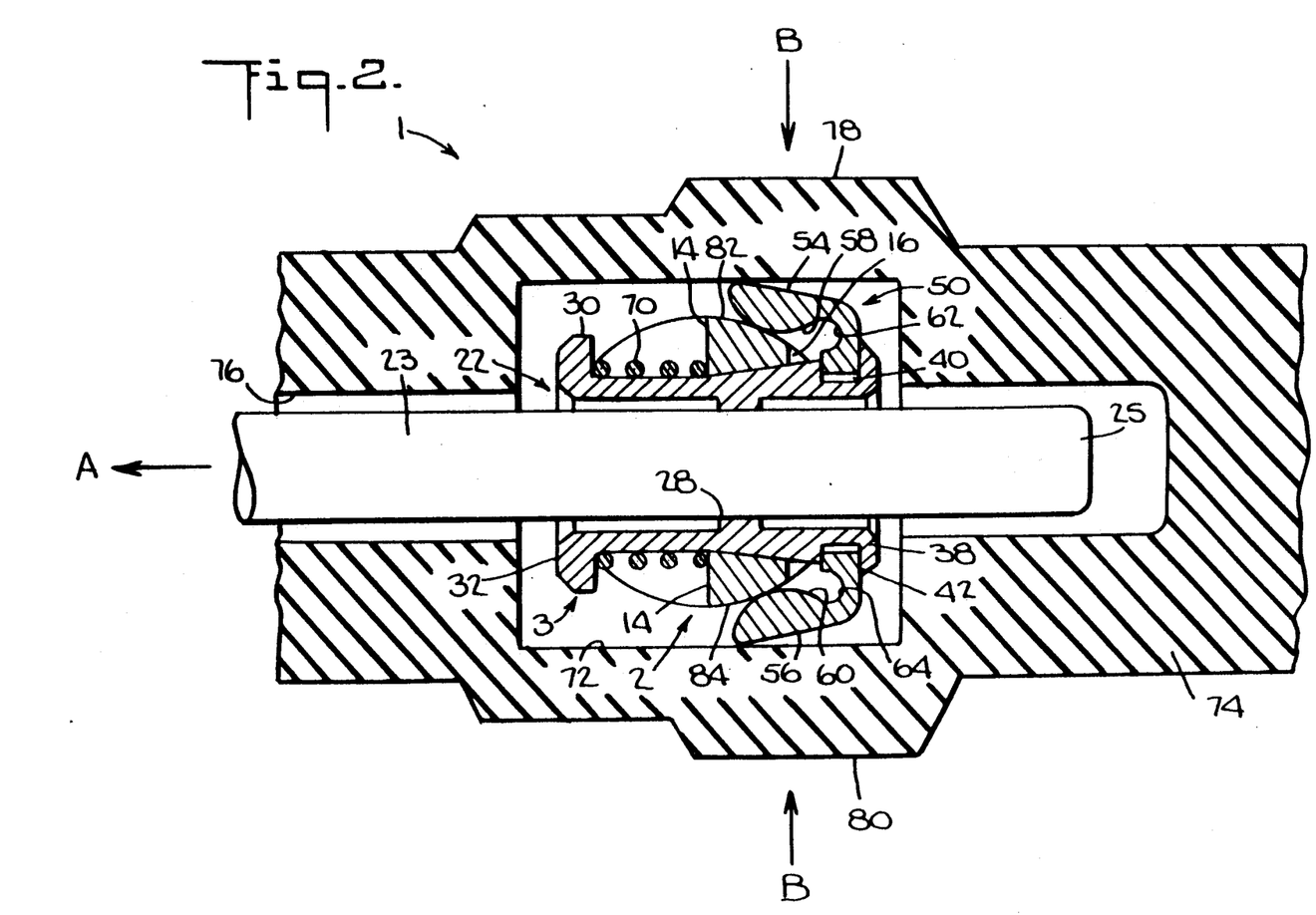
FIG. 2 is a cross-sectional view of the terminal shown in FIG. 1, in an assembled condition, with the proximal tip of an electrical lead inserted into, and being gripped by the terminal, and the terminal encapsulated inside an elastomeric sheath.

At this point, referring to FIG. 2, the assembly of terminal 1 is complete, and collet member 3 sits in post member 2 with its movable fingers 46 interlocked with release member 50. In addition, spring 70 is under compression between flange 30 of the collet member and the counterbored flat entrance side portion 14 of post member 2. In the final assembly of terminal 1, the terminal is positioned inside the cavity 72 of a molded sheath 74 of elastomeric material, preferably a bio-compatible silicone rubber, with the cylindrical axis of the collet member coinciding with the cylindrical axis of a molded self-sealing opening 76 in sheath 74. Sheath 74 is also provided with squeeze pads 78, 80 that are radially aligned with the leg portions 54, 56 of release member 50.

Assuming that terminal 1 has been fully assembled and that the proximal tip or pin 25 of electrode lead 23 has not yet been inserted into the terminal, the spring or biasing means 70 expanses fully and pushes the movable collet member 3 to the left, as viewed in FIG. 2, so that the conical portion 36 of the collet member engages the conical portion 12 of the stationary post member 2. The conical surfaces 36 and 12 interengage with one another during the movement to the left of the movable collet member 3 and, thus, the movable fingers or wall members 46 are cammed radially inwardly by the conical camming surface 12 acting against the conical cammed surface 36 during such movement. The inward camming of movable fingers 46 causes a reduction of the hole diameter of the ridge ring or middle portion 28 during that movement. In the absence of a proximal tip 25 of an electrode lead in the opening 22, the resulting diameter of the opening at the ridge ring 2 is reduced to a dimension that is less than the diameter of the proximal tip. The leftward movement of the movable structure 3 under the bias of spring 7 under such conditions is limited by the abutment of the base portion 52 of release member 50 against the side portion 16 of the stationary support structure 2. This position, and a position closely approaching it, wherein the leftward movement of the movable structure 3 is limited by the abutment of the ridge ring 28 against the outer perimeter of an inserted proximal tip 25 of an electrode lead, are hereinafter referred to as the "first position" of the movable structure of collet member 3. Thus the spring 70 serves as a means in engagement with both the movable structure and the stationary structure for biasing the movable structure toward its first position.

It will also be noted that when the movable collet member 3 is moving toward its first position, the curved inside camming surfaces 58, 60 on the leg portions 54, 56 of U-shaped release member 50 engage the cylindrical outer surfaces 82, 84, respectively, on opposite sides of the stationary post member 2. The leg portions 54 and 56 are thus cammed outwardly and remain in abutting contact with the respective cylindrical outer surfaces 82 and 84 when the collet member is in its first position.

In order to connect the proximal tip 25 to terminal 1, the proximal tip is inserted through the self-sealing opening 76 in the elastomeric sheath 74, into the aperture 22 of collet member 3, at the end 32 thereof. Because there is sufficient clearance between the tip and the entrance portion 24 of aperture 22, no interference occurs during the initial entry of the tip into the collet member. However, when the proximal tip 25 reaches the middle portion or ridge ring 28 of aperture 22, a controlled amount of sliding friction is generated between the tip 25 and the collet member 3 because of the smaller diameter of the ridge ring 28, which is an inwardly protruding ring section on the inner surface of aperture 22. Accordingly, collet member 2 starts to move to the right, as viewed in FIG. 3, toward a "second position" of the collet member, at which the conical surface 36 thereof partially disengages with the conical surface 12 of post member 2, allowing the movable fingers or wall members 46 to spring or flex radially outwardly and enlarge the diameter of the ridge ring or middle portion 28 of aperture 22.

Figure 3:
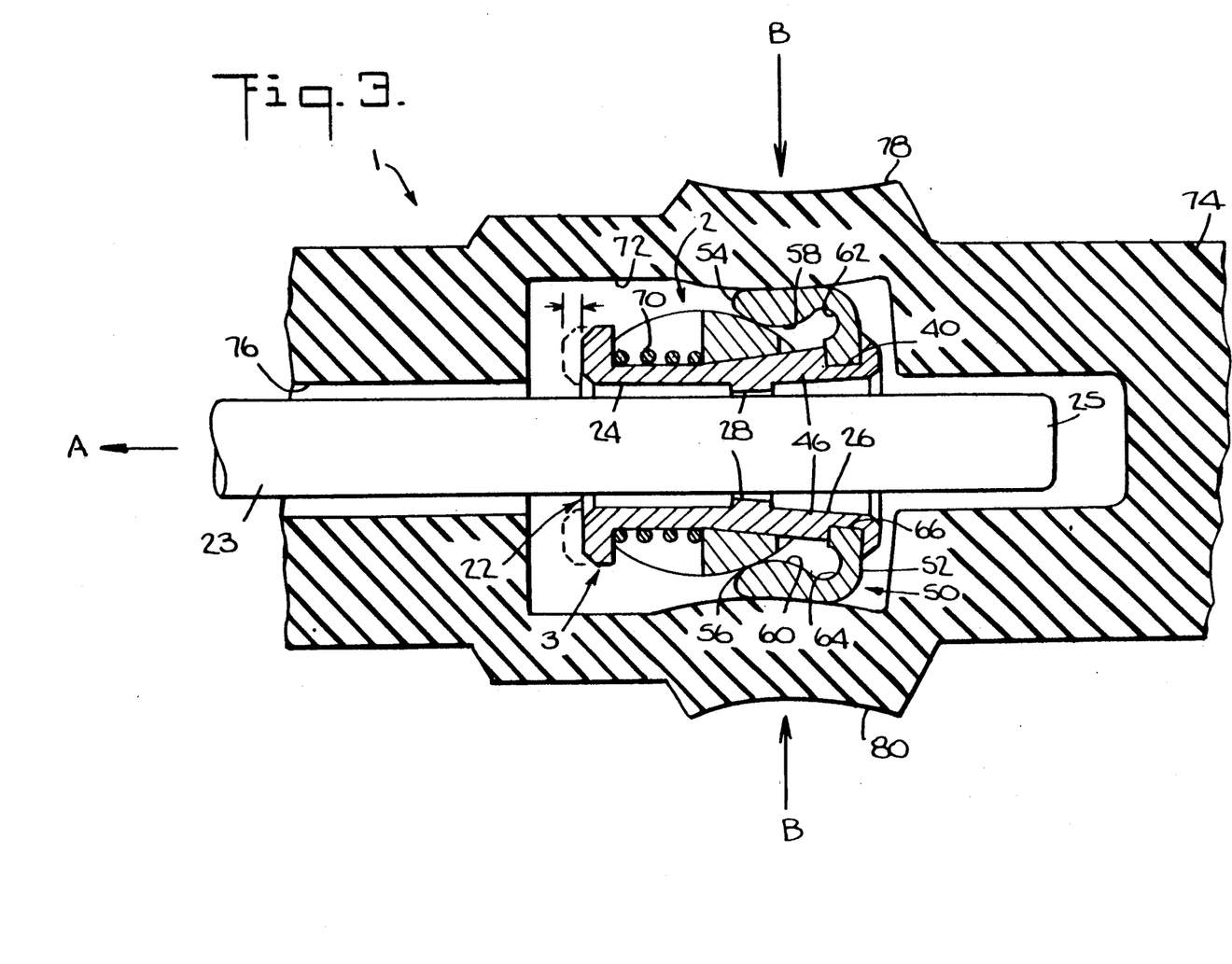
FIG. 3 is a view similar to FIG. 2, with the movable portion of the terminal actuated to release its grip on the proximal tip of the electrical lead in order to facilitate withdrawal of the lead from the terminal; and, FIGS. 4A, 4B and 4C are cross-sectional views of a movable portion of the terminal, showing the lead gripping interior surface thereof and various friction enhancing surfaces provided thereon.

Concurrently, the leg portions 54, 56 of release member 50 spring toward each other to a closer position, as shown in FIG. 3, and the spring 70 becomes compressed, all as shown in FIG. 3. This position of the movable structure or collet member 3 is hereinafter referred to as the "second position" of the movable structure 3. It can also be arrived at by the application of finger pressure against the squeeze pads 78 and 80 of sheath 74. This causes the leg portions 54 and 56 of release member 50 to move towards one another so that their camming surfaces 58, 60 react against the cylindrical surfaces 82 and 84 of stationary structure 2, moving release member 50 to the right, as viewed on FIGS. 2 and 3. This action also moves the remainder of movable structure 3 toward the right to the second position of the movable structure.

Assuming that the elastomeric sheath 74 is made of partially transparent or translucent silicone rubber, the proximal tip 25 of electrode lead 23 may be viewed through the sheath when it exits from the exit portion 26 of aperture 22. At this point, the surgeon stops inserting the tip of the lead and releases his grip on the lead. The ring of metal-to-metal contact between the tip 25 and the collet member 3 is maintained due to the bias of spring 70 and, after the surgeon's release of the electrical lead, spring 70 attempts to return to its fully-expanded position, pushing collet member 3 towards its first position and more fully re-engaging the conical surfaces 12 and 36 of the post member 2 and collet member 3, respectively. The movable fingers 46 on the collet member are thus squeezed to a closed position, and the two leg members 54, 56 on the release member 50 are pushed outward. At this stage, with the collet member back to its first position, the tip 25 is fully locked up in terminal 1, and electrical continuity is fully established between electrode lead 23 and terminal 1.

Accordingly, when there is an external pulling force A applied to the electrode lead to attempt to extract the proximal tip 25 from terminal 1, the contact interference at ridge ring 28 causes collet member 3 to travel in the same direction as the pulling force A, forcing the conical surface 36 formed by the movable fingers 46 to slide on and be cammed inwardly by the conical surface 12 of post member 1, thereby increasing the radially inward squeezing effect of the movable fingers 46. Consequently, a reactive force is generated at the contact ring between the ridge ring 28 and the electrode tip 25 which transforms into a static frictional force, preventing the tip 25 from sliding out of collet member 3. Preferably, the angle used on the conical surfaces 36 and 12 is chosen such that the static frictional force generated is always higher than the external pulling force. This assures that the tip remains securely fastened to the terminal, irrespective of the external pulling force applied.

In order to ensure that reliable electrical contact is maintained in terminal 1, spring 70 is always maintained under compression between the flange 30 of the collet member and the counterbored flat side portion 14 at the entrance of through hole 6 on post member 2. The movable fingers 46 of collet member 3 will thus be maintained in positive electrical contact with the proximal tip 25 at the ridge ring 28 because of the residual compressive spring force in the fingers 46 plus the extra compressive force generated by the spring 70 and converted by the camming mechanism between the two conical surfaces 12 and 36. Because of the floating design of the collet member 3 in post member 2, when an external pulling force A is applied to the electrode lead, the induced compressive force between the fingers 46 and the tip 25 will cause slight sliding movement, thereby enhancing the electrical contact.

As indicated earlier herein, when it is time to disconnect the electrode lead 23 from terminal 1, a gentle squeezing force B is applied to the squeeze pads 78, 80 on opposite sides of the elastomeric sheath 74. The squeezing force B deforms the elastomeric sheath and pushes the two leg portions 54, 56 of release member 50 inwardly toward each other. The inside round camming surfaces 58, 60 of the legs 54, 56 slide on the cylindrical surfaces 82, 84 of post member 2 and push the release member and the collet member attached thereto to the right, to the second position of the collet member, as shown in FIG. 3. This disengages the conical camming surfaces 12 and 36 from one another, causing the fingers 46 on collet member 2 to spring open and disengage the proximal tip 25 from the ridge ring 28. At this stage, the proximal tip 25 can be gently pulled out and disconnected from the terminal 1.

Figure 4A:
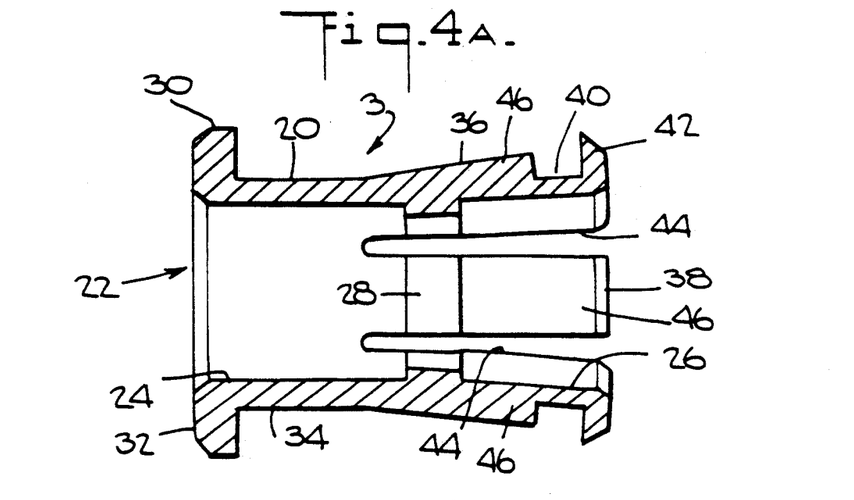
Figure 4B:
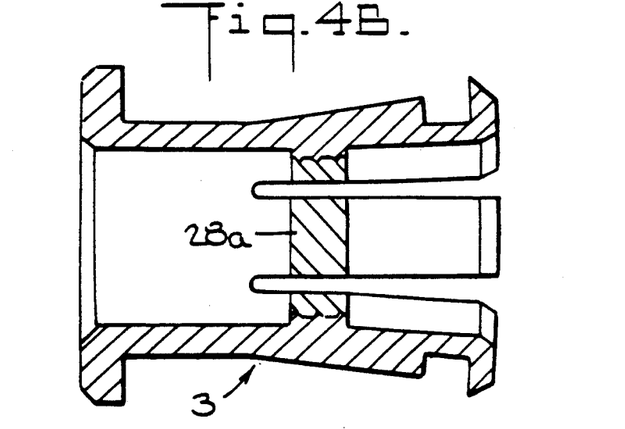
Figure 4C:
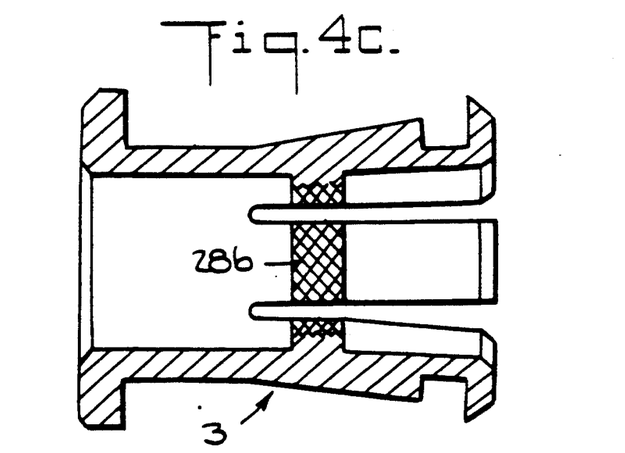

Referring to FIGS. 4B and 4C, alternate embodiments of the collet member 3 have there been shown. In the case of FIG. 4B, ridge ring 28a is provided with an internal thread thereon to further enhance the gripping characteristics of the ridge ring relative to the proximal tip 25 of the electrical lead. Similarly, in FIG. 4C, ridge ring 28b of collet member 3 is provided with a crisscross pattern of ridges and grooves to roughen the interior surface thereof to increase the gripping characteristics of the ridge ring.

It will apparent from the foregoing description that the terminal of this invention provides for the effortless, simple and reliable connection to it, and disconnection from it, of an electrical lead. When used as a pacemaker terminal, the invention eliminates the need for any special tools, including a set screw, for connecting and disconnecting the proximal tip of an electrode lead to the pacemaker terminal. In addition, the elimination of Allen wrench slits in the elastomeric sheath facilitate the prevention of body fluids from penetrating into the pacemaker terminal. Also, the improved terminal of the present invention provides for a reduction in the size of a pacemaker terminal, and in the overall dimensions of the elastomeric sheath used therewith.

While particular embodiments of this invention have been shown and described, it will be obvious to those skilled in the art that various other changes and modifications may be without departing from this invention in its broader aspects, and it is, therefore, aimed in the appended claims to cover all such changes and modifications as fall within the true spirit and scope of this invention.

I claim:

1. A terminal for detachably connecting an electrical lead to an electrical device, comprising:
   a support structure adapted to be fixed to said device;
   a movable structure adapted to be carried by said support structure for movement between first and second positions relative to said support structure, said movable structure having at least two wall members thereon movable relatively toward and away from one another between a first spaced apart position less than the diameter of said electrical lead and a second spaced apart position greater than the diameter of said electrical lead for receiving and releasing said lead in said second spaced apart position and for gripping said lead in said first spaced apart position;
   means for moving said movable structure between said first and second positions; and,
   first camming means carried by each of said structures and engageable with the camming means on the other of said structures for camming said wall members from one to another of said spaced apart positions.

2. A terminal according to claim 1, further including means in engagement with both of said structures for biasing said movable structure toward one or the other of said first and second positions.

3. A terminal according to claim 1, wherein when said movable structure is in said first position, said wall members are in said first spaced apart position, and when said movable structure is in said second position said wall members are in said second spaced apart position.

4. A terminal according to claim 3, wherein said movable structure moving means includes means in engagement with each of said structures for biasing said movable structure toward one or the other of said first and second positions.

5. A terminal according to claim 4, wherein said biasing means biases said movable structure toward said first position to maintain a grip on said lead in the absence of a bias overcoming force that tends to move said movable structure from said first position to said second position.

6. A terminal according to claim 5, wherein said movable structure moving means includes hand-operated second camming means for moving said movable structure in opposition to said biasing means from said first position to said second position.

7. A terminal according to any one of claims 1-6, wherein said movable structure comprises an annular collet member having an elongate axial opening extending therethrough, said axial opening being of greater diameter than the diameter of said electrical lead, said collet member having a circumferentially continuous, generally cylindrical, first portion and a circumferentially interrupted, generally conical second portion, and wherein said wall members comprise a plurality of cantilevered axially elongate fingers each integral at corresponding ones of their ends with said first portion of said collet member, said fingers being positioned adjacent one another about said elongate axial opening to form said second portion of said collet member, the radially inner portions of said fingers forming a continuation of said elongate axial opening at said greater diameter when said fingers are in an unflexed condition, the radially outer portions of said fingers comprising a continuation of the outer surface of said first portion of said collet member and flaring radially outwardly to form said generally conical second portion of said collet member, said fingers being sufficiently flexible that the radially inward portions of the free end portions thereof can be flexed radially inwardly to reduce the diameter of said axial opening in said second portion of said collet member to one that is less than the diameter of said electric lead for gripping said lead in said second portion.

8. A terminal according to claim 7, wherein said support structure comprises an elongate post member having a length greater than its width, and an aperture-forming wall that extends transversely therethrough, said aperture having a first predetermined diameter adjacent one end thereof, a second predetermined diameter smaller than said first predetermined diameter at a location therein spaced from said one end, and a generally conical surface portion extending between said location and said one end.

9. A terminal according to claim 8, wherein said collet member is movably positioned in said aperture of said post member, and wherein said first camming means includes said conical surface portion of said aperture-forming wall of said post member and said conical second portion of said collet member.

10. A terminal according to claim 9, wherein said post member includes opposite side portions, and wherein said collet member extends outwardly of said opposite side portions, said collet member further including an enlarged flange at the end of said first portion thereof opposite the end thereof that is integral with said fingers, the diameter of said flange being greater than the diameter of said aperture in said post member, and radially outwardly extending flange-forming protrusions at the free end portions of said fingers, and wherein said second camming means includes means engageable with said free end portions of said fingers and with said post member for limiting movement of said collet member relative to said post member under the bias of said biasing means.

11. A terminal according to claim 10, wherein said biasing means comprising a cylindrical spring surrounding said cylindrical first portion of said collet member and having one of its ends abutting against said enlarged flange of said collet member and the other of its ends abutting against one of said side portions of said post member to bias said collet member toward its first position.

12. A terminal according to claim 10, wherein the radially outer surfaces of said free end portions of said fingers are provided with circumferentially extending radially inwardly directed grooves, and wherein said movement limiting means of said second camming means includes a retainer member having an aperture therein adapted to receive said free end portions of said fingers, said retainer member being adapted to seat in said grooves of said free end portions.

13. A terminal according to claim 12, wherein said biasing means comprises a cylindrical spring surrounding said cylindrical first portion of said collet member and having one of its ends abutting against said enlarged flange of said collet member and the other of its ends abutting against one of said side portions of said post member to bias said collet member toward its first position.

14. A terminal according to claim 13, wherein the radially inner surfaces of said fingers are provided with ridges to increase the gripping characteristics of said fingers relative to said electrical lead when said collet member is in its first position.

15. A terminal according to claim 12, wherein said retainer member is U-shaped in form and includes a base portion and a pair of leg portions flexibly attached thereto which engage said post member when said collet member is in its first position, and wherein said aperture of said retainer member is formed in said base portion and said base portion seats in said grooves of said free end portion of said fingers.

16. In combination, a terminal as described in claim 8, said terminal being for use in connecting the proximal end of an electrode lead to an implantable heart pacemaker, and a silicone rubber sheath surrounding and sealingly enclosing said terminal, said sheath having a self-sealing opening therein coaxial with the axis of said elongate axial opening of said collet member.

17. In combination, a terminal as described in claim 7, said terminal being for use in connecting the proximal end of an electrode lead to an implantable heart pacemaker, and a silicone rubber sheath surrounding and sealingly enclosing said terminal, said sheath having a self-sealing opening therein coaxial with the axis of said elongate axial opening of said collet member.

18. A terminal according to any one of claims 1-6, wherein said support structure comprises an elongate post member having a length greater than its width, and an aperture-forming wall that extends transversely therethrough, said aperture having a first predetermined diameter adjacent one end thereof, a second predetermined diameter smaller than said first predetermined diameter at a location therein spaced from said one end, and a generally conical surface portion extending between said location and said one end.

19. A terminal according to any one of claims 1-6, wherein during movement of said movable structure from said second position to said first position static frictional forces are generated by said first camming means for gripping said electrical lead at said first position, wherein said moving means moves said movable structure relative to said support structure along a longitudinal axis, wherein said first camming means includes at least one camming surface that is so angularly related to said axis that when said movable structure is gripping said electrical lead at said first position and a pulling force is applied to said lead tending to pull said lead out of said terminal, said first camming means generates additional static friction forces that increase the grip on said electrical lead sufficiently to overcome said pulling force and retain said lead securely fastened to said terminal.

20. A terminal according to claim 19, wherein said movable structure comprises an annular collet member having an elongate axial opening extending therethrough, said axial opening being of greater diameter than the diameter of said electrical lead, said collet member having a circumferentially continuous, generally cylindrical, first portion and a circumferentially interrupted, generally conical second portion, said generally conical second portion comprising said at least one camming surface, and wherein said wall members comprise a plurality of cantilevered axially elongate fingers each integral at corresponding ones of their ends with said first portion of said collet member, said fingers being positioned adjacent one another about said elongate axial opening to form said second portion of said collet member, the radially inner portions of said fingers forming a continuation of said elongate axial opening at said greater diameter when said fingers are in an unflexed condition, the radially outer portions of said fingers comprising a continuation of the outer surface of said first portion of said collet member and flaring radially outwardly to form said generally conical second portion of said collet member, said fingers being sufficiently flexible that the radially inward portions of the free end portions thereof can be flexed radially inwardly to reduce the diameter of said axial opening in said second portion of said collet member to one that is less than the diameter of said electrical lead for gripping said lead in said second portion.

21. A terminal according to claim 20, wherein said support structure comprises an elongate post member having a length greater than its width, and an aperture-forming wall that extends tranversely therethrough, said aperture having a first predetermine diameter adjacent one end thereof, a second predetermined diameter smaller than said first predetermined diameter at a location therein spaced from said one end, and a generally conical surface portion extending between said location and said one end, said generally conical surface portion comprising a second camming surface that is inclined to said axis at the same angle as that of said at least one camming surface.

22. A terminal according to claim 21, wherein said collet member is movably positioned in said aperture of said post member, and wherein said first camming means includes said conical surface portion of said aperture-forming wall of said post member and said conical second portion of said collet member.

23. A terminal according to claim 19, wherein said support structure comprises an elongate post member having a length greater than its width, and an aperture-forming wall that extends tranversely therethrough, said aperture having a first predetermined diameter adjacent one end thereof, a second predetermined diameter smaller than said first predetermined diameter at a location therein spaced from said one end, and a generally conical surface portion extending between said location and said one end, said generally conical surface portion comprising said at least one camming surface.

24. A terminal for connecting and releasing by hand pressure the proximal end of an electrode lead to an implantable heart pacemaker, comprising:

an elongate post member adapted to be fixed to said pacemaker, said post member having a length greater than its width and an aperture forming wall that extends tranversely therethrough, said aperture having a first predetermined diameter adjacent one end thereof, a second predetermined diameter less than said first predetermined diameter at a location spaced from said one end, and a generally conical surface portion extending between said location and said one end;

an elongate collet member having a flange adjacent one end thereof and a length greater than the width of said post member, said collet member being receivable in the aperture of said post member with said flange adjacent one side portion of said post member, and the other end of said collet member extending beyond an opposite side portion of said post member, said collet member having an aperture extending longitudinally therethrough adapted to receive the end of said electrode lead therein, said collet member being axially movable between first and second spaced apart positions and including means cooperable with said conical surface portion of said aperture wall and engageable with said lead when said collet member is in said first position for locking said lead to said collet member;

means in engagement both with said flange of said collet member and said one side portion of said post member for biasing said collet member toward said first position; and, means engageable both with said other end of said collet member and with said post member and adapted to be squeezed by hand pressure for moving said collet member to its second position and releasing said lead from the grip of said collet member.

25. A terminal according to claim 24, and further including an elastomeric sheath surrounding and sealingly enclosing said terminal, said sheath having a self-sealing opening therein coaxial with the axis of said longitudinal aperture of said collet member.

* * * * *

UNITED STATES PATENT AND TRADEMARK OFFICE
CERTIFICATE OF CORRECTION

PATENT NO. : 5,069,209

DATED : December 3, 1991

INVENTOR(S) : Jack Posin (sic)

It is certified that error appears in the above-identified patent and that said Letters Patent is hereby corrected as shown below:

On the cover page of the patent, change the name of the inventor from "Jack Posin" to -- Arthur Kin-Wai Yee --.

Signed and Sealed this

Twenty-third Day of March, 1993

*Attest:*

STEPHEN G. KUNIN

*Attesting Officer*      *Acting Commissioner of Patents and Trademarks*